(12) United States Patent
Prior et al.

(10) Patent No.: US 11,857,216 B2
(45) Date of Patent: Jan. 2, 2024

(54) SYSTEMS AND METHODS FOR LARGE TISSUE SPECIMEN REMOVAL

(71) Applicant: Covidien LP, Mansfield, MA (US)

(72) Inventors: Scott J. Prior, Branford, CT (US); Paul C. DiCesare, Easton, CT (US); Richard A. Cronenberg, Mahwah, NJ (US)

(73) Assignee: Covidien LP, Mansfield, MA (US)

( * ) Notice: Subject to any disclaimer, the term of this patent is extended or adjusted under 35 U.S.C. 154(b) by 200 days.

(21) Appl. No.: 17/398,282

(22) Filed: Aug. 10, 2021

(65) Prior Publication Data

US 2021/0361319 A1 Nov. 25, 2021

Related U.S. Application Data

(62) Division of application No. 16/108,444, filed on Aug. 22, 2018, now Pat. No. 11,083,490.
(Continued)

(51) Int. Cl.
*A61B 17/34* (2006.01)
*A61B 17/00* (2006.01)
(Continued)

(52) U.S. Cl.
CPC .... *A61B 17/3421* (2013.01); *A61B 17/00234* (2013.01); *A61B 2017/00287* (2013.01);
(Continued)

(58) Field of Classification Search
CPC . A61B 17/34; A61B 17/3417; A61B 17/3421; A61B 17/3423; A61B 17/3439;
(Continued)

(56) References Cited

U.S. PATENT DOCUMENTS 5,643,283 A 7/1997 Younker
6,059,793 A 5/2000 Pagedas
(Continued)

FOREIGN PATENT DOCUMENTS

WO 2004002334 A1 1/2004
WO 2014158880 A1 10/2014

*Primary Examiner* — Ashley L Fishback
(74) *Attorney, Agent, or Firm* — Carter, DeLuca & Farrell LLP

(57) ABSTRACT

A system includes an access cannula, a deployment cannula having a plurality of engagement arms, and a containment bag. The deployment cannula is slidable within the access cannula between an initial condition, wherein the engagement arms are retained in a contracted configuration, and a deployed condition, wherein the engagement arms are disposed in an expanded configuration. The containment bag includes an open end portion configured to receive the first elongated tubular member and the second elongated tubular member. In the initial condition, a portion of the containment bag towards the open end portion is positioned adjacent at least one of the first elongated tubular member or the second elongated tubular member. In the deployed condition, the portion of the containment bag is expanded such that the portion of the containment bag is spaced-apart from the at least one of the first elongated tubular member or the second elongated tubular member.

14 Claims, 7 Drawing Sheets

Related U.S. Application Data

(60) Provisional application No. 62/561,231, filed on Sep. 21, 2017.

(51) Int. Cl.
*A61B 17/3207* (2006.01)
*A61B 17/32* (2006.01)

(52) U.S. Cl.
CPC ............. *A61B 2017/320024* (2013.01); *A61B 2017/320775* (2013.01); *A61B 2017/3484* (2013.01); *A61B 2017/3486* (2013.01)

(58) Field of Classification Search
CPC ............ A61B 17/3431; A61B 17/8819; A61B 17/00234; A61B 17/00218; A61B 17/0469; A61B 17/12013; A61B 17/1285; A61B 17/320016; A61B 2017/349; A61B 2017/20047; A61B 2017/3425; A61B 2017/3427; A61B 2017/3433; A61B 2017/3447; A61B 2017/00287; A61B 2017/320024; A61B 2017/320775; A61B 2017/3484; A61B 2017/3486
See application file for complete search history.

(56) References Cited

U.S. PATENT DOCUMENTS

| | | | |
|---|---|---|---|
| 6,156,055 A | 12/2000 | Ravenscroft | |
| 6,162,209 A | 12/2000 | Gobron et al. | |
| 6,171,317 B1 | 1/2001 | Jackson et al. | |
| 6,206,889 B1 | 3/2001 | Bennardo | |
| 6,224,612 B1 | 5/2001 | Bates et al. | |
| 6,228,095 B1 | 5/2001 | Dennis | |
| 6,248,113 B1 | 6/2001 | Fina | |
| 6,251,119 B1 * | 6/2001 | Addis .............. | A61B 17/3415 606/167 |
| 6,258,102 B1 | 7/2001 | Pagedas | |
| 6,264,663 B1 | 7/2001 | Cano | |
| 6,270,505 B1 | 8/2001 | Yoshida et al. | |
| 6,280,451 B1 | 8/2001 | Bates et al. | |
| 6,344,026 B1 | 2/2002 | Burbank et al. | |
| 6,350,266 B1 | 2/2002 | White et al. | |
| 6,350,267 B1 | 2/2002 | Stefanchik | |
| 6,358,198 B1 | 3/2002 | Levin et al. | |
| 6,368,328 B1 | 4/2002 | Chu et al. | |
| 6,383,195 B1 | 5/2002 | Richard | |
| 6,383,197 B1 | 5/2002 | Conlon et al. | |
| 6,387,102 B2 | 5/2002 | Pagedas | |
| 6,406,440 B1 | 6/2002 | Stefanchik | |
| 6,409,733 B1 | 6/2002 | Conlon et al. | |
| 6,447,523 B1 | 9/2002 | Middleman et al. | |
| 6,530,923 B1 | 3/2003 | Dubrul et al. | |
| 6,537,273 B1 | 3/2003 | Sosiak et al. | |
| 6,752,822 B2 | 6/2004 | Jespersen | |
| 6,805,699 B2 | 10/2004 | Shimm | |
| 6,951,533 B2 | 10/2005 | Foley | |
| 6,986,774 B2 | 1/2006 | Middleman et al. | |
| 7,037,275 B1 | 5/2006 | Marshall et al. | |
| 7,052,501 B2 | 5/2006 | McGuckin, Jr. | |
| 7,087,062 B2 | 8/2006 | Dhindsa | |
| 7,101,379 B2 | 9/2006 | Gregory, Jr. et al. | |
| 7,101,380 B2 | 9/2006 | Khachin et al. | |
| 7,112,172 B2 | 9/2006 | Orban, III et al. | |
| 7,115,125 B2 | 10/2006 | Nakao et al. | |
| 7,144,400 B2 | 12/2006 | Byrum et al. | |
| 7,169,154 B1 | 1/2007 | Que et al. | |
| 7,229,418 B2 | 6/2007 | Burbank et al. | |
| 7,285,126 B2 | 10/2007 | Sepetka et al. | |
| 7,316,692 B2 | 1/2008 | Huffmaster | |
| 7,357,801 B2 | 4/2008 | Burbank et al. | |
| 7,534,252 B2 | 5/2009 | Sepetka et al. | |
| 7,547,310 B2 | 6/2009 | Whitfield | |
| 7,615,013 B2 | 11/2009 | Clifford et al. | |
| 7,618,437 B2 | 11/2009 | Nakao | |
| 7,645,283 B2 | 1/2010 | Reynolds et al. | |
| 7,670,346 B2 | 3/2010 | Whitfield | |
| 7,678,118 B2 | 3/2010 | Bates et al. | |
| 7,722,626 B2 | 5/2010 | Middleman et al. | |
| 7,727,227 B2 | 6/2010 | Teague et al. | |
| 7,731,722 B2 | 6/2010 | Lavelle et al. | |
| 7,731,723 B2 | 6/2010 | Kear et al. | |
| 7,762,959 B2 | 7/2010 | Bilsbury | |
| 7,762,960 B2 | 7/2010 | Timberlake et al. | |
| 7,875,038 B2 | 1/2011 | Que et al. | |
| 7,892,242 B2 | 2/2011 | Goldstein | |
| 7,914,540 B2 | 3/2011 | Schwartz et al. | |
| 7,918,860 B2 | 4/2011 | Leslie et al. | |
| 7,955,292 B2 | 6/2011 | Leroy et al. | |
| 8,057,485 B2 | 11/2011 | Hollis et al. | |
| 8,075,567 B2 | 12/2011 | Taylor et al. | |
| 8,118,816 B2 | 2/2012 | Teague | |
| 8,152,820 B2 | 4/2012 | Mohamed et al. | |
| 8,172,772 B2 | 5/2012 | Zwolinski et al. | |
| 8,211,115 B2 | 7/2012 | Cheng et al. | |
| 8,282,572 B2 | 10/2012 | Bilsbury | |
| 8,337,510 B2 | 12/2012 | Rieber et al. | |
| 8,348,827 B2 | 1/2013 | Zwolinski | |
| 8,409,216 B2 | 4/2013 | Parihar et al. | |
| 8,414,596 B2 | 4/2013 | Parihar et al. | |
| 8,419,749 B2 | 4/2013 | Shelton, IV et al. | |
| 8,425,533 B2 | 4/2013 | Parihar et al. | |
| 8,430,826 B2 | 4/2013 | Uznanski et al. | |
| 8,435,237 B2 | 5/2013 | Bahney | |
| 8,444,655 B2 | 5/2013 | Parihar et al. | |
| 8,486,087 B2 | 7/2013 | Fleming | |
| 8,512,351 B2 | 8/2013 | Teague | |
| 8,579,914 B2 | 11/2013 | Menn et al. | |
| 8,585,712 B2 | 11/2013 | O'Prey et al. | |
| 8,591,521 B2 | 11/2013 | Cherry et al. | |
| 8,652,147 B2 | 2/2014 | Hart | |
| 8,721,658 B2 | 5/2014 | Kahle et al. | |
| 8,734,464 B2 | 5/2014 | Grover et al. | |
| 8,777,961 B2 | 7/2014 | Cabrera et al. | |
| 8,795,291 B2 | 8/2014 | Davis et al. | |
| 8,821,377 B2 | 9/2014 | Collins | |
| 8,827,968 B2 | 9/2014 | Taylor et al. | |
| 8,870,894 B2 | 10/2014 | Taylor et al. | |
| 8,906,035 B2 | 12/2014 | Zwolinski et al. | |
| 8,956,370 B2 | 2/2015 | Taylor et al. | |
| 8,968,329 B2 | 3/2015 | Cabrera | |
| 8,986,321 B2 | 3/2015 | Parihar et al. | |
| 9,005,215 B2 | 4/2015 | Grover et al. | |
| 9,017,328 B2 | 4/2015 | Bahney | |
| 9,017,340 B2 | 4/2015 | Davis | |
| 9,033,995 B2 | 5/2015 | Taylor et al. | |
| 9,084,588 B2 | 7/2015 | Farascioni | |
| 9,101,342 B2 | 8/2015 | Saleh | |
| 9,113,848 B2 | 8/2015 | Fleming et al. | |
| 9,113,849 B2 | 8/2015 | Davis | |
| 9,308,008 B2 | 4/2016 | Duncan et al. | |
| 9,364,201 B2 | 6/2016 | Orban, III | |
| 9,364,202 B2 | 6/2016 | Menn et al. | |
| 9,370,341 B2 | 6/2016 | Ceniccola et al. | |
| 9,370,378 B2 | 6/2016 | O'Prey et al. | |
| 9,375,224 B2 | 6/2016 | Jansen | |
| 9,414,817 B2 | 8/2016 | Taylor et al. | |
| 9,468,452 B2 | 10/2016 | Menn et al. | |
| 9,486,188 B2 | 11/2016 | Secrest et al. | |
| 9,522,034 B2 | 12/2016 | Johnson et al. | |
| 9,549,747 B2 | 1/2017 | Carlson | |
| 9,579,115 B2 | 2/2017 | Kahle et al. | |
| 9,592,067 B2 | 3/2017 | Hartoumbekis | |
| 9,622,730 B2 | 4/2017 | Farascioni | |
| 9,629,618 B2 | 4/2017 | Davis et al. | |
| 9,642,638 B1 | 5/2017 | Carrier | |
| 9,655,644 B2 | 5/2017 | Collins | |
| 9,730,716 B2 | 8/2017 | Secrest et al. | |
| 9,789,268 B2 | 10/2017 | Hart et al. | |
| 9,808,228 B2 | 11/2017 | Kondrup et al. | |
| 9,826,997 B2 | 11/2017 | Cherry et al. | |
| 9,867,600 B2 | 1/2018 | Parihar et al. | |
| 9,877,893 B2 | 1/2018 | Taylor et al. | |

(56) References Cited

U.S. PATENT DOCUMENTS

| | | | |
|---|---|---|---|
| 2002/0022850 A1* | 2/2002 | McGuckin, Jr. | ............................ A61B 17/320016 606/114 |
| 2009/0205643 A1 | 8/2009 | Tanaka et al. | |
| 2011/0184430 A1* | 7/2011 | Parihar | ............ A61B 17/00234 606/114 |
| 2013/0006282 A1 | 1/2013 | Wilkinson | |
| 2013/0317534 A1 | 11/2013 | Zhou et al. | |
| 2014/0188126 A1* | 7/2014 | Odon | ................... A61B 17/442 606/122 |
| 2015/0297209 A1 | 10/2015 | Piskun | |
| 2016/0166243 A1 | 6/2016 | Wilson | |
| 2017/0215904 A1* | 8/2017 | Wassef | ................... A61B 17/32 |
| 2017/0245839 A1* | 8/2017 | Malkowski | ...... A61B 17/32002 |

* cited by examiner

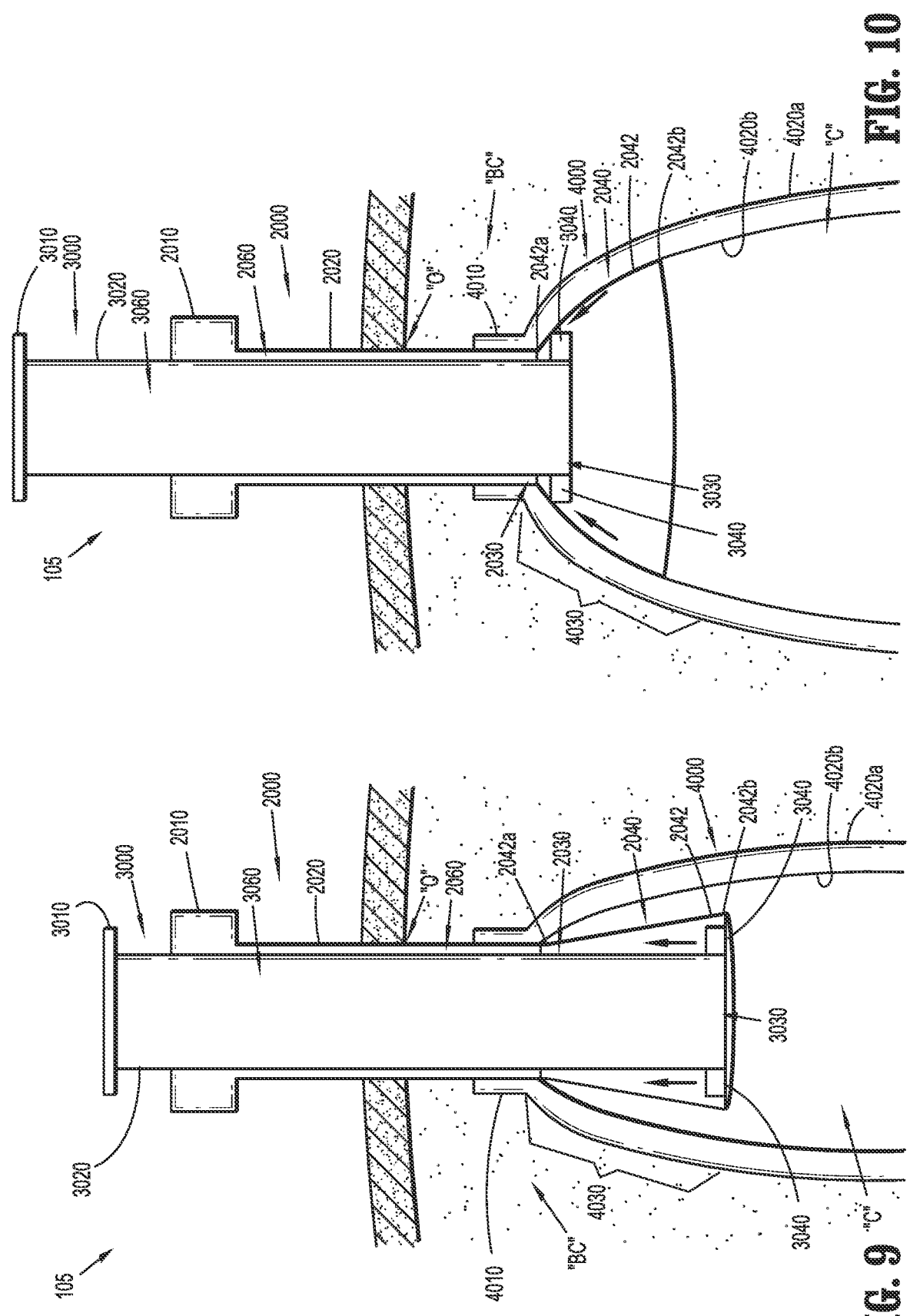

SYSTEMS AND METHODS FOR LARGE TISSUE SPECIMEN REMOVAL

CROSS-REFERENCE TO RELATED APPLICATIONS

The present application is a divisional of U.S. patent application Ser. No. 16/108,444, filed on Aug. 22, 2018, now U.S. Pat. No. 11,083,490, which claims the benefit of and priority to, U.S. Provisional Patent Application No. 62/561,231, filed Sep. 21, 2017. The entire contents of each of the foregoing applications are hereby incorporated by reference herein.

BACKGROUND

Technical Field

The present disclosure relates to tissue specimen removal and, more particularly, to systems and methods facilitating removal of a large tissue specimen from an internal body cavity using a containment bag.

Background of Related Art

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total removal of tissue from an internal body cavity. However, the restricted access provided by minimally-invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down using a surgical instrument, e.g., morcellator or another cutting device, into a plurality of smaller pieces to facilitate removal from the internal body cavity.

During such minimally-invasive surgical procedures, it is common that a cyst, tumor, or other affected tissue is required to be removed. In these and other procedures where cancerous tissue is required to be removed, removal of the tissue specimen(s) in an enclosed environment is highly desirable to inhibit seeding of cancer cells. Thus, with respect to breaking down large tissue specimens for removal through minimally-invasive openings, there is the added challenge of doing so within an enclosed environment without compromising the structural integrity of the enclosed environment.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a system for removal of a tissue specimen from an internal body cavity. The system includes an access cannula, a deployment cannula, and a containment bag. The access cannula includes a first elongated tubular member and defines a lumen extending through the first elongated tubular member. The deployment cannula includes a second elongated tubular member and a port guard assembly having a plurality of engagement arms. Each of the plurality of engagement arms has a proximal end portion hingedly coupled to the second elongated tubular member and a distal end portion hingedly coupled to the second elongated tubular member. The deployment cannula is configured for slidable positioning within the access cannula and movable relative thereto between an initial condition and a deployed condition. In the initial condition, the plurality of engagement arms is retained in a contracted configuration wherein the plurality of engagement arms extend adjacent the second elongated tubular member. In the deployed condition, the plurality of engagement arms is disposed in an expanded configuration wherein the plurality of engagement arms extend radially-outwardly from the second elongated tubular member. The containment bag includes an open end portion configured to receive the first elongated tubular member and the second elongated tubular member. In the initial condition, a portion of the containment bag towards the open end portion thereof is positioned adjacent at least one of the first elongated tubular member or the second elongated tubular member. In the deployed condition, the portion of the containment bag is engaged by the plurality of engagement arms and urged radially-outwardly such that the portion of the containment bag is spaced-apart from the at least one of the first elongated tubular member or the second elongated tubular member.

In an aspect of the present disclosure, the access cannula may include a proximal hub disposed at a proximal end of the first elongated tubular member and the deployment cannula may include a proximal hub disposed at a proximal end of the second elongated tubular member. In such aspects, in the initial condition, the proximal hub of the deployment cannula may be positioned proximally adjacent the proximal hub of the access cannula, and in the deployed condition, the proximal hub of the deployment cannula may be proximally-spaced from the proximal hub of the access cannula.

In another aspect of the present disclosure, each of the plurality of engagement arms may include a first arm portion hingedly coupled to a second arm portion. In such aspects, upon movement from the initial condition towards the deployed condition, the second arm portion may be moved towards the first arm portion.

In another aspect of the present disclosure, the port guard assembly may further include a cuff coupled to the second elongated tubular member of the deployment cannula adjacent an open distal mouth thereof. In such aspects, the second arm portion of each of the plurality of engagement arms may be hingedly coupled to the cuff.

In yet another aspect of the present disclosure, the plurality of engagement arms may be biased radially outwardly such that, in the deployed condition, the plurality of engagement arms may be returned under bias to urge the portion of the containment bag radially outwardly.

Provided in accordance with another aspect of the present disclosure is a system for removal of a tissue specimen from an internal body cavity. The system includes an access cannula and a containment bag. The access cannula includes a first elongated tubular member and a port guard assembly having a plurality of engagement fingers. Each of the plurality of engagement fingers is engaged to the first elongated tubular member at a fixed end thereof and extending to a free end thereof. In an initial condition, the plurality of engagement fingers is retained in a contracted configuration wherein each of the plurality of engagement fingers extend alongside the first elongated tubular member. In a deployed condition, the free end of each of plurality engagement fingers extends radially outwardly from the first elongated tubular member. The containment bag includes an open end portion configured to receive the first elongated tubular member of the access cannula. In the initial condition, a portion of the containment bag is positioned adjacent the first elongated tubular member. In the deployed condition, the portion of the containment bag is engaged by the plurality of engagement fingers and urged radially outwardly such that the portion is spaced-apart from the first elongated tubular member.

In still another aspect of the present disclosure, the system further may include an introducer having a second elongated tubular member. In such aspects, the second elongated tubular member may have a first introducer portion configured to selectively couple to a second introducer portion to define a lumen extending through the second elongated tubular member. In such aspects, the lumen may be configured to selectively retain the access cannula and the containment bag in the initial condition.

In another aspect of the present disclosure, the plurality of fingers may be biased radially-outwardly from the first elongated tubular member such that, in the initial condition, the plurality of fingers may be retained in the contracted configuration in the lumen of the introducer against the bias of the plurality of fingers.

In yet another aspect of the present disclosure, in the deployed condition, the first introducer portion may be configured to selectively decouple from the second introducer portion such that, the access cannula may be released from the lumen of the introducer and the free ends of each of plurality engagement fingers may be radially-outwardly returned under the bias thereof.

In still another aspect of the present disclosure, in the initial condition, the containment bag may be disposed within an annular space defined within the lumen of the introducer between the second elongated tubular member and the first elongated tubular member. In such aspects, in the deployed condition, the containment bag may be deployed from the lumen of the introducer under the bias of the plurality of engagement fingers.

In yet another aspect of the present disclosure, the port guard assembly may further include an inflatable member disposed on the first elongated tubular member and engaged with the plurality of engagement fingers. In such aspects, the inflatable member may have a deflated configuration in the initial condition and an inflated configuration in the deployed condition. In such aspects, in the inflated configuration, the inflatable member may be configured to engage the plurality of engagement fingers and urge the free ends of each of plurality engagement fingers radially-outwardly.

In still yet another aspect of the present disclosure, the inflatable member may be disposed on the first elongated tubular member distal to the fixed ends of each of the plurality of engagement fingers such that the plurality of engagement fingers extend distally along an exterior surface of the inflatable member.

In an aspect of the present disclosure, the inflatable member may include a lumen configured to receive the elongated tubular member of the access cannula.

In another aspect of the present disclosure, the inflatable member may include an interior cavity configured to be in fluid communication with the elongated tubular member of the access cannula such that the inflatable member is selectively inflatable via the access cannula.

Provided in accordance with another aspect of the present disclosure is a system for removal of a tissue specimen from an internal body cavity. The system includes an access cannula, a deployment cannula, and a containment bag. The access cannula includes a first elongated tubular member and a port guard assembly having a plurality of petals. Each of the plurality of petals is engaged to the first elongated tubular member at a fixed end thereof and extending to a free end thereof. In an initial condition, the plurality of petals is disposed in a contracted configuration wherein each of the plurality of petals is positioned to overlap adjacent petals of the plurality of petals. In a deployed condition, the plurality of petals is configured to be disposed in an expanded configuration wherein the plurality of petals is expanded radially outwardly. The deployment cannula includes a second elongated tubular member and a camming boss. The deployment cannula is configured for slidably positioning within the access cannula and movable relative thereto between the initial condition, wherein the plurality of petals is disposed in the contracted configuration and the deployed condition, wherein the plurality of petals is disposed in the expanded configuration. The containment bag includes an open end portion configured to receive the first elongated tubular member and the second elongated tubular member. In the initial condition, a portion of the containment is positioned adjacent at least one of the first elongated tubular member or the second elongated tubular member. In the deployed condition, the portion of the containment bag is engaged by the plurality of petals and urged radially outwardly such that the portion is spaced-apart from at least one of the first elongated tubular member or the second elongated tubular member.

In another aspect of the present disclosure, each of the plurality of petals may overlap with adjacent petals of the plurality of petals.

In yet another aspect of the present disclosure, the camming boss may include a plurality of tabs spaced-apart and disposed on an exterior surface of the second elongated tubular member.

In still another aspect of the present disclosure, the plurality of petals may include a base layer of petals and a top layer of petals. In such aspects, in the initial condition, the base layer of petals may be disposed adjacent the exterior surface of the second elongated tubular member and the top layer of petals may be folded over and disposed adjacent the base layer of petals.

In another aspect of the present disclosure, as the deployment cannula moves relative to the access cannula towards the deployed condition, the camming boss may be configured to move along an interior surface of the base layer of petals towards the fixed ends of the plurality of petals.

In yet another aspect of the present disclosure, movement of the camming boss towards the fixed ends of the plurality of petals may be configured to engage the base layer of petals and urge the base layer of petals radially outwardly to thereby urge the top layer of petals radially outwardly such that the plurality of petals is radially-outwardly spaced from the second elongated tubular member.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements and:

FIG. 9 is a side, longitudinal, partial cross-sectional view of another tissue specimen removal system provided in accordance with the present disclosure, disposed in an initial condition and extending through an opening in tissue into an internal body cavity;

FIG. 10 is a side, longitudinal, partial cross-sectional view of the tissue specimen removal system of FIG. 9, disposed in a deployed condition and extending through an opening in tissue into an internal body cavity;

DETAILED DESCRIPTION

The present disclosure provides devices, systems, and methods facilitating removal of a large tissue specimen from an internal body cavity while maintaining the large tissue specimen in an enclosed environment during break down and removal from the internal body cavity.

Figure 1A:
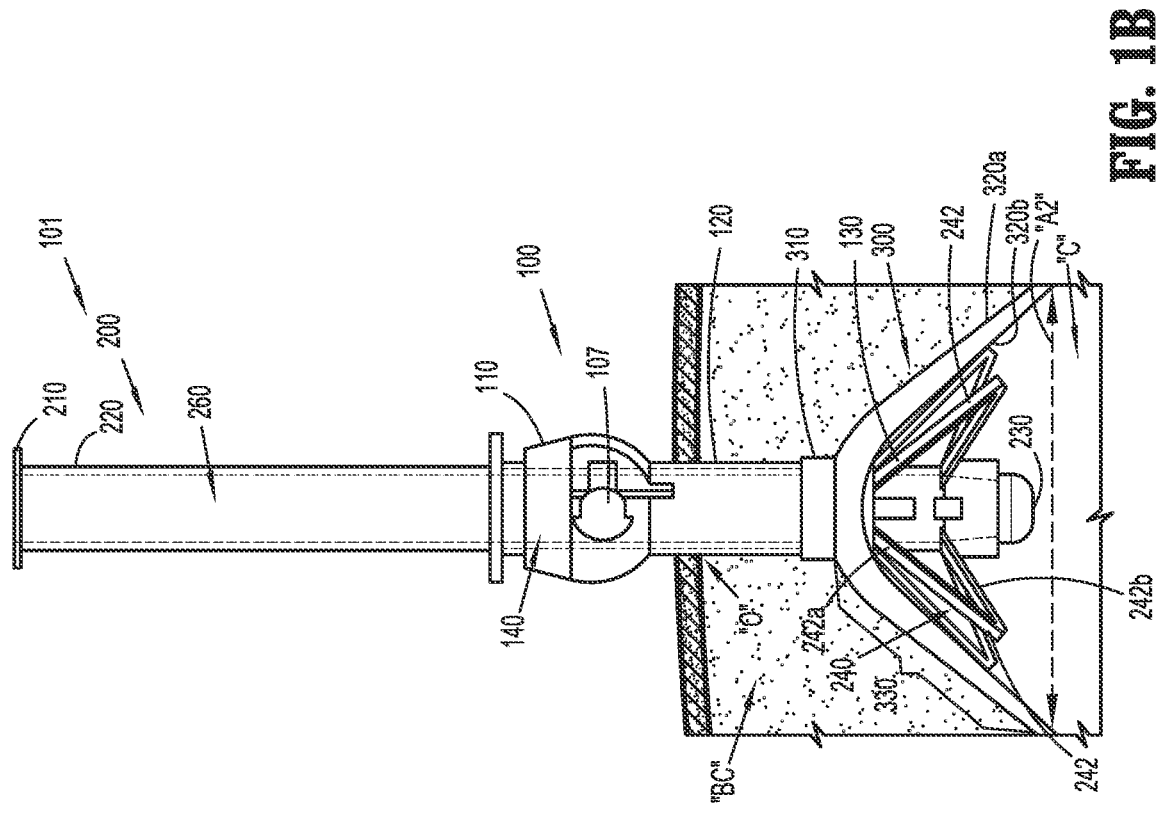
FIG. 1A is a side, longitudinal, partial cross-sectional view of a tissue specimen removal system provided in accordance with the present disclosure, disposed in an initial condition and extending through an opening in tissue into an internal body cavity.
Figure 1B:
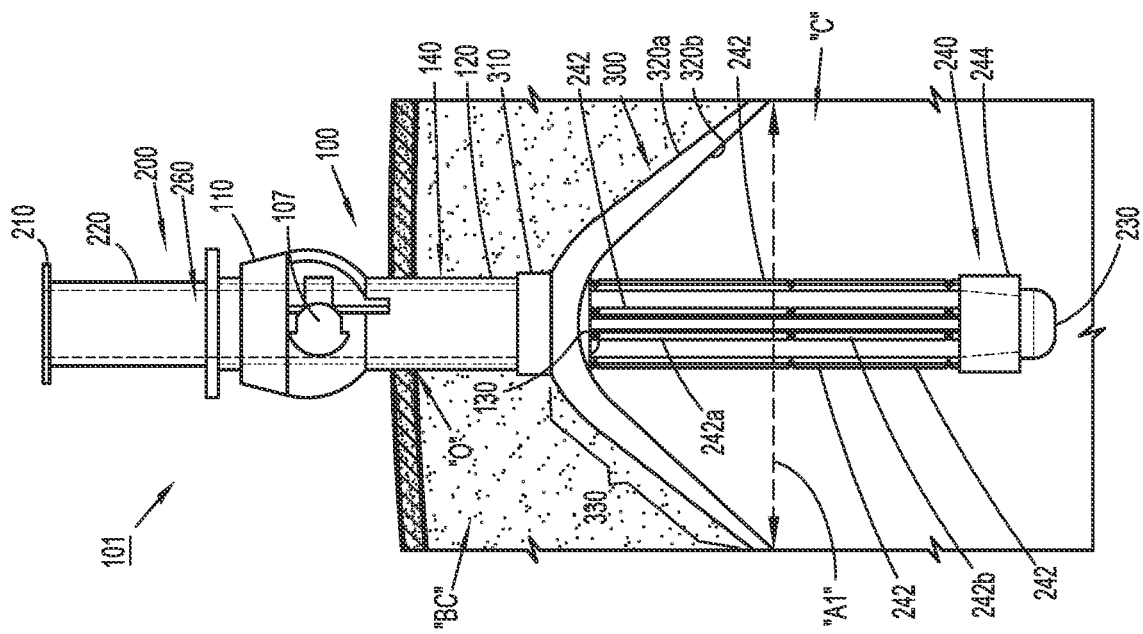
FIG. 1B is a side, longitudinal, partial cross-sectional view of the tissue specimen removal system of FIG. 1A, disposed in a deployed condition and extending through an opening in tissue into an internal body cavity.

Turning initially to FIGS. 1A and 1B, a specimen retrieval system 101 provided in accordance with the present disclosure generally includes an outer assembly, such as, for example, an access cannula 100, an inner assembly, such as, for example, a deployment cannula 200, and a containment bag 300. Access cannula 100 includes a proximal hub 110, an elongated tubular member 120, and an open distal mouth 130. A lumen 140 extends through proximal hub 110 and elongated tubular member 120, in communication with open distal mouth 130, to enable the insertion of deployment cannula 200, and, in some embodiments, other surgical instruments, through access cannula 100 and into a cavity "C" of containment bag 300 via an open end portion 310 of containment bag 300.

Proximal hub 110 of access cannula 100 is configured to remain externally-disposed and may include an insufflation port 107 to enable the introduction of insufflation fluid through lumen 140 and into the internal body cavity to insufflate the internal body cavity. To this end, proximal hub 110 may further include one or more seals (not shown) configured to seal lumen 140 in the absence of deployment cannula 200, containment bag 300, and/or other surgical instruments inserted therethrough, and/or to establish a seal about deployment cannula 200, containment bag 300, and/or other surgical instruments inserted through lumen 140, in order to maintain the internal body cavity in an insufflated condition.

Elongated tubular member 120 of access cannula 100 is configured to extend through a surgically created or naturally occurring opening "O" into an internal body cavity "BC" such that open distal mouth 130 is at least partially disposed within internal body cavity "BC," while proximal hub 110 remains externally disposed. Open distal mouth 130 of access cannula 100 is configured to facilitate atraumatic insertion of elongated tubular member 120 through the surgically created or naturally occurring opening "O" and into the internal body cavity. In embodiments, open distal mouth 130 of access cannula 100 may include a beveled or other suitable configuration.

Continuing with reference to FIGS. 1A and 1B, deployment cannula 200 includes a proximal hub 210, an elongated core, such as, for example, a tubular member 220, an open distal mouth 230, and a port guard assembly 240.

A lumen 260 extends through proximal hub 210 and elongated tubular member 220, in communication with open distal mouth 230, to enable the insertion of surgical instruments through deployment cannula 200 and into cavity "C" of containment bag 300 via open end portion 310 of containment bag 300. Deployment cannula 200 is configured for slidable positioning within lumen 140 of access cannula 100 and may be positioned therein in an initial condition (FIG. 1A) during manufacturing or may be inserted into access cannula 100 by a user.

Proximal hub 210 of deployment cannula 200 is configured to remain externally-disposed relative to the internal surgical site and access cannula 100. More specifically, in an initial condition (FIG. 1A) of specimen retrieval system 101, proximal hub 210 of deployment cannula 200 is positioned proximally adjacent proximal hub 110 of access cannula 100. In a deployed condition (FIG. 1B), on the other hand, proximal hub 210 of deployment cannula 200 is proximally-spaced from proximal hub 110 of access cannula 100, although it is also contemplated that this configuration be reversed. It is further contemplated that at least a portion of tubular member 220 is retained within lumen 140 of access cannula 100 when specimen retrieval system 101 is moved between the initial and deployed conditions.

Similarly, as with proximal hub 110 of access cannula 100, proximal hub 210 of deployment cannula 200 may include one or more seals (not shown) configured to seal lumen 260 in the absence of surgical instruments inserted therethrough and/or to establish a seal about surgical instruments inserted through lumen 260, in order to maintain the internal body cavity in an insufflated condition. Proximal hub 210 of deployment cannula 200 may also include an insufflation port (not shown) to enable the introduction of insufflation fluid through lumen 260 to, for example, insufflate containment bag 300.

Tubular member 220 of deployment cannula 200 is configured to extend through lumen 140 of access cannula 100 and into cavity "C" of containment bag 300. More specifically, tubular member 220 defines a suitable length so as to enable proximal hub 210 of deployment cannula 200 to remain externally disposed of the internal body cavity and access cannula 100 while a distal end of elongated tubular member 220 extends to or beyond open distal mouth 130 of access cannula 100.

Port guard assembly 240 includes a plurality of engagement arms 242 having a first arm portion 242a hingedly coupled to a second arm portion 242b. Further, a proximal end portion of first arm portion 242a is hingedly coupled to an exterior surface of tubular member 220 and a distal end portion of second arm portion 242b is hingedly coupled to a cuff 244 that is coupled to the exterior surface of tubular member 220, proximally adjacent open distal mouth 230 thereof. The plurality of engagement arms 242 may be radially-spaced about a circumference of cuff 244, although any suitably configuration for the plurality of engagement arms 242 may be provided.

The various hinge couplings detailed above may include living hinges, pivot-pin hinges, or other suitable hinge arrangements to enable the plurality of engagement arms 242 to transition between a contracted configuration and an expanded configuration. Specifically, in the initial condition (FIG. 1A) of specimen retrieval system 101, wherein tubular member 220 of deployment cannula 200 is disposed within lumen 140 of access cannula 100 and proximal hub 210 of deployment cannula 200 is positioned proximally adjacent proximal hub 110 of access cannula 100, engagement arms 242 are retained in the contracted configuration, wherein engagement arms 242 extend alongside the exterior of tubular member 220 to define a generally linear configuration, thus enabling engagement arms 242 and tubular member 220 to fit within lumen 140 of access cannula 100. Once deployment cannula 200 is moved proximally relative to access cannula 100 towards the deployed condition (FIG. 1B) of specimen retrieval system 101, the proximal end portions of first arm portions 242a of the engagement arms 242 are pushed against open distal mouth 130 of access cannula 100 and the distal end portions of the second arm portions 242b of the engagement arms 242 are moved towards the proximal end portions of first arm portions 242a such that, engagement arms 242, lead by the hinges coupling the respective first and second arm portions 242a, 242b thereof, flex or expand outward from the exterior surface of tubular member 220 to the expanded configuration. In embodiments, in the deployed condition (FIG. 1B) of specimen retrieval system 101 and, thus, the expanded configuration of engagement arms 242, engagement arms 242 may be positioned to define a basket-like configuration. In the deployed condition, port guard assembly 240 is configured to engage and provide structural support to containment bag 300 to maintain containment bag 300 spaced-apart from distal mouth 230 of deployment cannula 200, as detailed below.

It is contemplated that engagement arms 242 may be biased radially-outwardly from elongated tubular member 220 towards the expanded configuration of engagement arms 242 such that, in the initial condition of specimen retrieval system 101 (FIG. 1A), engagement arms 242 are retained, against their bias, in the contracted configuration. In embodiments, engagement arms 242 may be formed from a spring-metal, e.g., spring steel, although other suitable materials, e.g., nitinol, are also contemplated. Further, as an alternative to providing deployment cannula 200 with engagement arms 242, engagement arms 242 may be disposed on another surgical instrument to be used within the internal body cavity such as, for example, a morcellator (not shown). An exemplary morcellator for this purpose is described in Patent Application Publication No. US 2015/0073429, filed on Jun. 12, 2014, the entire contents of which are hereby incorporated herein by reference.

With continued reference to FIGS. 1A and 1B, containment bag 300 includes an outer surface 320a, an inner surface 320b, and cavity "C" defined by inner surface 320b and configured to enable positioning of a tissue specimen(s) therein. Further, as described above, containment bag 300 includes open end portion 310 configured to receive at least a portion of access cannula 100 and deployment cannula 200 within cavity "C" of containment bag 300. In the initial condition (FIG. 1A) of specimen retrieval system 101, with containment bag 300 deployed about access cannula 100 and deployment cannula 200, a top portion 330 of containment bag 300 disposed towards open end portion 310, may be positioned substantially adjacent open distal mouths 130, 230 of access cannula 100 and deployment cannula 200, respectively, in contact therewith or to define a first annular space "A1" therebetween. In the deployed condition (FIG. 1B) of specimen retrieval system 101, with containment bag 300 deployed about access cannula 100 and deployment cannula 200, engagement arms 242 of port guard assembly 240 expand outward from the exterior surface of tubular member 220 and are configured to engage inner surface 320b of containment bag 300 adjacent top portion 330 of containment bag 300 and to urge top portion 330 of containment bag 300 radially outwardly relative to access cannula 100 and deployment cannula 200. As such, the engagement arms 242 ensure that top portion 330 of containment bag 300 is maintained radially spaced-apart from open distal mouths 130, 230 of access cannula 100 and deployment cannula 200, respectively, to define a minimum second annular space "A2" therebetween that is greater than first annular space "A1."

In the deployed condition (FIG. 1B) of specimen retrieval system 101, port guard assembly 240 is configured to prevent top portion 330 of containment bag 300 from collapsing about open distal mouths 130, 230 of access cannula 100 and deployment cannula 200, respectively, as detailed above. More specifically, port guard assembly 240 is configured to serve as a spacer between top portion 330 of containment bag 300 and open distal mouths 130, 230 of access cannula 100 and deployment cannula 200, respectively, such that, one or more surgical instrument(s) 2 (FIG. 2B) inserted through deployment cannula 200 and access cannula 100, and into cavity "C" of containment bag 300, are inhibited from contacting inner surface 320b adjacent the top portion 330 of containment bag 300. In embodiments, surgical instrument 2 may be a morcellator or another cutting device. In such embodiments, port guard assembly 240 is configured to inhibit contact between the morcellator or the another cutting device and inner surface 320b adjacent the top portion 330 of containment bag 300 to inhibit cutting or tearing of containment bag 300.

Containment bag 300 may define any suitable configuration such as, for example, a circular, dogleg, L-shape, C-shape, or other suitable configuration. The particular configuration of containment bag 300 may depend upon the desired access location and/or the procedure to be performed. Containment bag 300 may be formed from any suitable material. In particular, containment bag 300 may be formed from a transparent, tear-resistant, stretchable material to enable visualization into containment bag 300 from the exterior thereof, inhibit tearing, and facilitate manipulation of containment bag 300, tissue specimen(s), and/or surgical instruments 2 during use.

Open end portion 310 of containment bag 300 may include features (not shown) to facilitate sealed closure thereof such as, for example, a threaded lip configured to receive a screw-on cap, or may be configured to be sealed closed by way of a suture, clip, cord, or other suitable mechanism or method. Open end portion 310 may be configured to receive a tissue specimen therethrough and into cavity "C" of containment bag 300. Alternatively or additionally, containment bag 300 may include one or more other openings (not explicitly shown) in addition to open end portion 310 to facilitate insertion of a tissue specimen therethrough and into cavity "C" of containment bag 300. These other openings may likewise include features similar to those of open end portion 310 to facilitate sealed closure thereof.

Figure 2A:
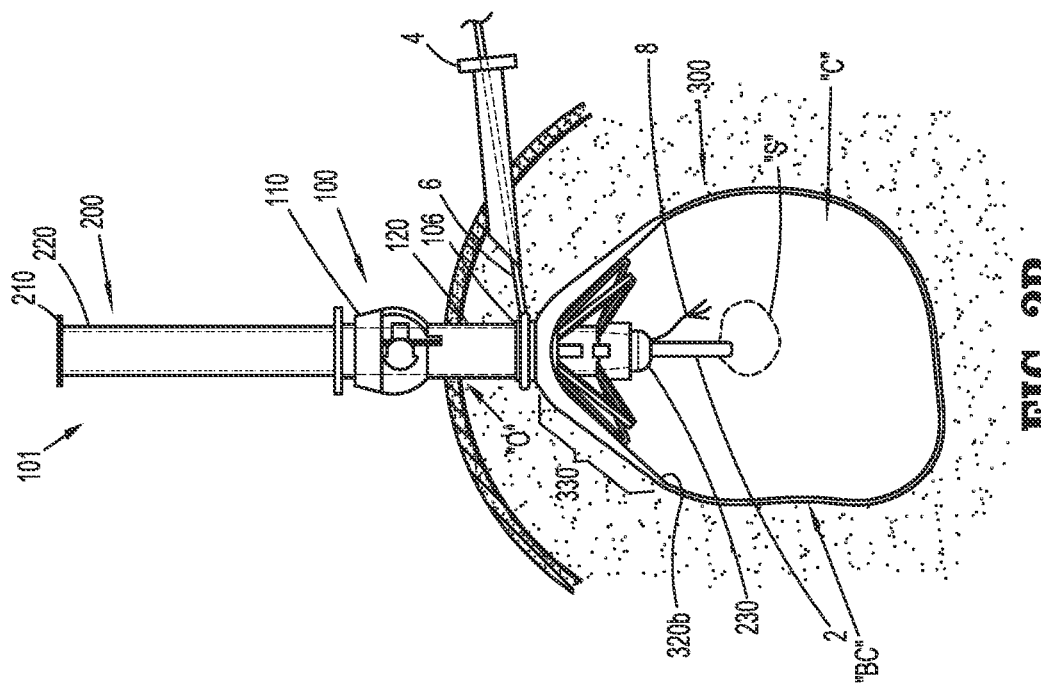
FIG. 2A is a side, longitudinal, partial cross-sectional view of the tissue specimen removal system of FIG. 1A, disposed in the initial condition, illustrating enclosure of a tissue specimen within the containment bag.
Figure 2B:
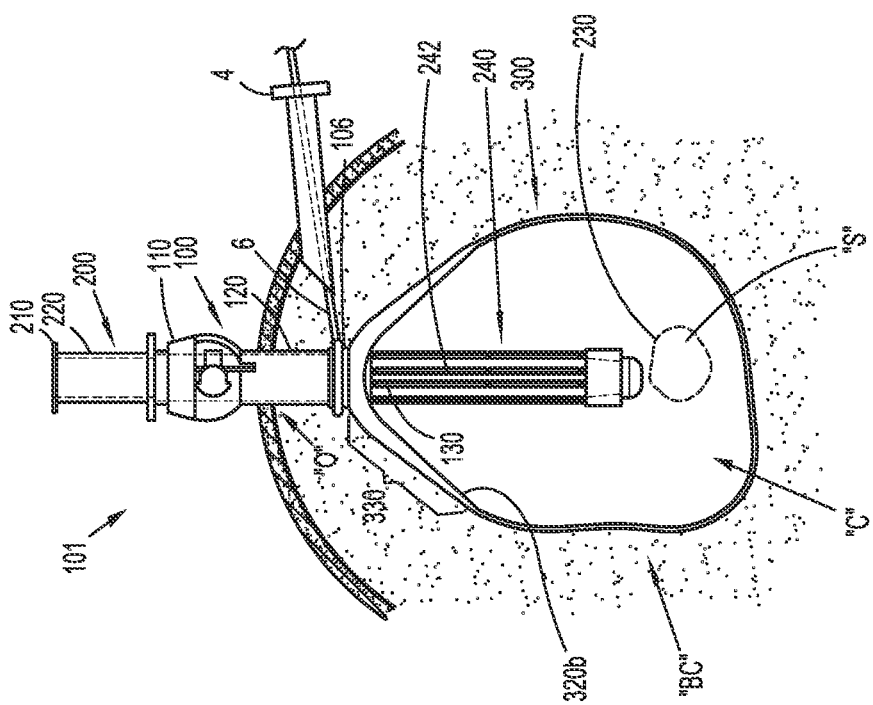
FIG. 2B is a side, longitudinal, partial cross-sectional view of the tissue specimen removal system of FIG. 1B, disposed in the deployed condition, illustrating break down of the tissue specimen to enable removal from the internal body cavity.

With reference to FIGS. 2A and 2B, in conjunction with FIGS. 1A and 1B, the use of specimen retrieval system 101 in the removal of a tissue specimen "S" from internal body cavity "BC" is described. Specimen retrieval system 101 may be similarly used in the removal of other tissue specimen from other internal body cavities.

Referring first to FIG. 2A, with deployment cannula 200 disposed within access cannula 100 and proximal hub 210 of deployment cannula 200 positioned proximally adjacent proximal hub 110 of access cannula 100 such that engagement arms 242 are retained in the contracted configuration (FIG. 1A), access cannula 100 and deployment cannula 200 are advanced through surgically created or naturally occurring opening "O" into internal body cavity "BC." Access cannula 100 and deployment cannula 200 may be inserted directly or may be inserted through a port (not shown). Additionally or alternatively, insertion of access cannula 100 and deployment cannula 200 may be facilitated through the use of a trocar (not shown) disposed within or about access cannula 100 or deployment cannula 200.

Continuing with FIG. 2A, Containment bag 300 may be inserted into internal body cavity "BC" via a port 4, and may be deployed about elongated tubular member 120 of access cannula 100 and tubular member 220 of deployment cannula 200 using a suitable deployment apparatus 6. Alternatively, containment bag 300 and deployment apparatus 6 may be operably disposed about elongated tubular member 120 of access cannula 100 towards open distal mouth 130 thereof, or may be coupled to an outer deployment tube (not shown) disposed about elongated tubular member 120, to enable containment bag 300 to be deployed distally from elongated tubular member 120 about open distal mouth 130.

Once deployed into or otherwise disposed within the internal body cavity "BC," containment bag 300 and/or the tissue specimen "S" are manipulated, e.g., using a grasper (not shown) inserted through deployment cannula 200 or another port (not shown), to position the tissue specimen "S" within cavity "C" of containment bag 300. Thereafter or prior thereto, if not already so positioned (such as, for example, in embodiments where containment bag 300 is deployed from access cannula 100), open end portion 310 (FIG. 1A) of containment bag 300 is positioned to surround open distal mouths 130, 230 of access cannula 100 and deployment cannula 200, respectively. Open end portion 310 of containment bag 300 may then be cinched or otherwise secured about open distal mouth 130 of access cannula 100 to form a substantially fluid-tight seal, thereby sealing open distal mouths 130, 230 of access cannula 100 and deployment cannula 200, respectively, within cavity "C" of containment bag 300. To this end, an annular divot 106 may be defined within the exterior surface of elongated tubular member 120 of access cannula 100 towards open distal mouth 130 thereof to facilitate cinching the open end portion 310 of containment bag 300 about elongated tubular member 120 of access cannula 100 and to "lock" the open end portion 310 of containment bag 300 in position about elongated tubular member 120.

In embodiments, containment bag 300 may be positioned within internal body cavity "BC" prior to advancing access cannula 100 and deployment cannula 200 into internal body cavity "BC." Specifically, once containment bag 300 is disposed within internal body cavity "BC" and tissue specimen "S" is positioned within cavity "C" of containment bag 300, open end portion 310 of containment bag 300 may be exteriorized from internal body cavity "BC" through opening "O." Next, open distal mouths 130, 230 of access cannula 100 and deployment cannula 200, respectively, may be advanced through opening "O" and open end portion 310 of containment bag 300 and into within cavity "C" of containment bag 300. Finally, open end portion 310 of containment bag 300 may be cinched or otherwise secured about open distal mouth 130 of access cannula 100 in the manner described above, or may remain open, externally of the body cavity "BC."

Turning to FIG. 2B, with containment bag 300 sealed about open distal mouth 130 of elongated tubular member 120 of access cannula 100, or externalized from the body cavity "BC," such that open distal mouths 130, 230 of access cannula 100 and deployment cannula 200, respectively, are disposed within cavity "C" of containment bag 300, deployment cannula 200 may be moved proximally relative to access cannula 100 towards the deployed condition (FIG. 1B) of specimen retrieval system 101 such that, engagement arms 242 of port guard assembly 240 expand outward from the exterior surface of tubular member 220 and engage inner surface 320b adjacent top portion 330 of containment bag 300, urging top portion 330 of containment bag 300 radially outwardly to maintain top portion 330 of containment bag 300 spaced-apart from open distal mouths 130, 230. Once specimen retrieval system 101 is in the deployed condition, surgical instrument 2 may be inserted through deployment cannula 200 (and, thus, through access cannula 100) such that surgical instrument 2 extends from open distal mouth 230 of deployment cannula 200 and is disposed adjacent tissue specimen "S." Surgical instrument 2 may then be used to morcellate or otherwise act on the tissue specimen "S," for example, to break down the tissue specimen "S" into smaller pieces to facilitate removal. In embodiments, surgical instrument 2 may include any suitable dimension (e.g., diameter) configured for a particular purpose, for example, to maximize the resection rate of tissue specimen "S."

As detailed above, damage to containment bag 300 from contact with surgical instrument 2 during insertion, breakdown of the tissue specimen "S," and removal, is inhibited by virtue of engagement arms 242 of port guard assembly 240 maintaining top portion 330 of containment bag 300 spaced-apart from open distal mouths 130, 230. Surgical instrument 2 may also include one or more feature(s) configured to control the extension of a distal end thereof beyond open distal mouth 230 of deployment cannula 200. It is contemplated that limiting the extension of the distal end of surgical instrument 2 to a position, for example, where a cutting edge of surgical instrument 2 is disposed just below port guard assembly 240 would ensure that surgical instrument 2 is not advanced too far into containment bag 300, thereby inhibiting surgical instrument 2 from inadvertently cutting or tearing containment bag 300 opposite top portion 330 thereof. In order to position tissue specimen "S" adjacent surgical instrument 2, a user may utilize a tenaculum (not shown) or the like, to move tissue specimen "S" towards surgical instrument 2.

Continuing with FIG. 2B, a visualization device 8 may be utilized to facilitate breakdown of the tissue specimen "S." Visualization device 8 may include a laparoscope or the like, and have any suitable dimension (e.g., 5 mm diameter laparoscope). In embodiments, visualization device 8 may be inserted through deployment cannula 200 (and, thus, through access cannula 100) via a lumen (not shown) separate from lumen 260 used for the insertion of surgical instrument 2. Alternatively, visualization device 8 may be inserted through access cannula 100 via a lumen (not shown) separate from lumen 140 used for the insertion of deployment cannula 200. Visualization device 8 may also be disposed within internal body cavity "BC" via a secondary port (not shown) and disposed within containment bag 300 via a secondary opening (not shown). In embodiments where containment bag 300 is formed from a transparent material, visualization device 8 may be disposed within internal body cavity "BC" and remain external of containment bag 300 while providing a view of cavity "C" of containment bag 300. Visualization device 8 may include an articulating scope (not shown) configured to facilitate maneuverability as well as visibility within body cavity "BC" and cavity "C" of containment bag 300.

Once the tissue specimen "S" is sufficiently broken down, surgical instrument 2 and visualization device 8 may be removed from cavity "C" of containment bag 300 and from internal body cavity "BC". Thereafter, access cannula 100 and deployment cannula 200 are returned (fully or partially) towards the initial condition (FIG. 1A) of specimen retrieval system 101, wherein engagement arms 242 are in the contracted configuration alongside the exterior of tubular member 220 of deployment cannula 200. Further, containment bag 300 may be released from its deployment apparatus 6 to enable withdrawal of access cannula 100 together with containment bag 300 from internal body cavity "BC." Alternatively, in embodiments where containment bag 300 is removable from elongated tubular member 210 of access cannula 100, containment bag 300 may be released therefrom after engagement arms 242 are contracted such that access cannula 100 and deployment cannula 200 may be removed through the opening "O" while containment bag 300 may be removed through port 4.

Figure 4:
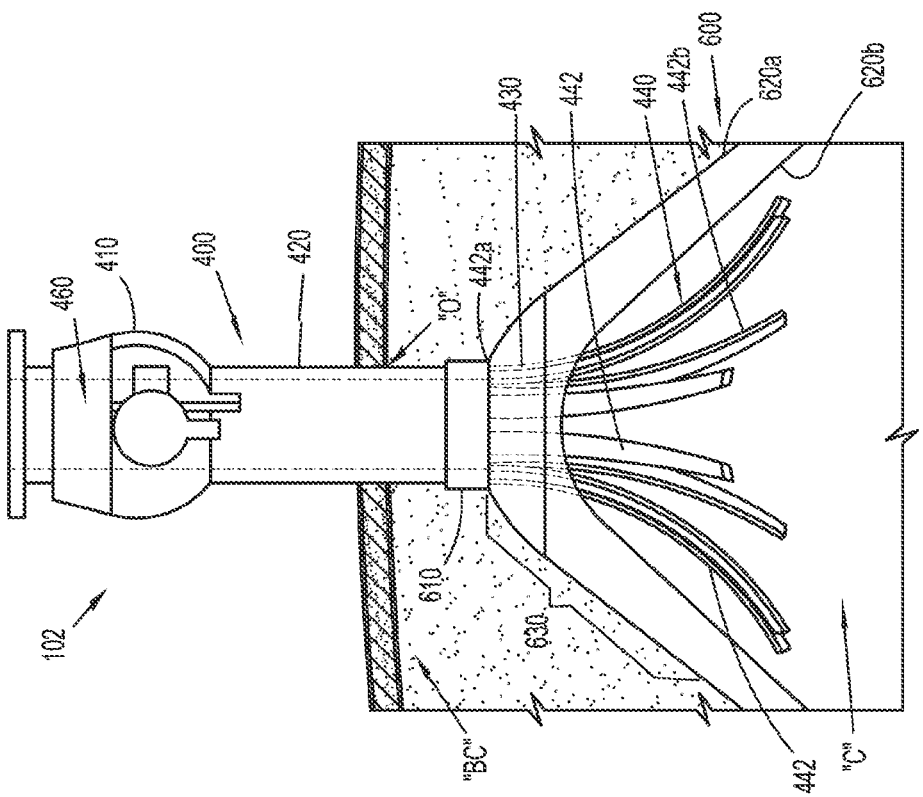
FIG. 4 is a side, longitudinal, partial cross-sectional view of the tissue specimen removal system of FIG. 3, disposed in a deployed condition and extending through an opening in tissue into an internal body cavity.
Figure 3:
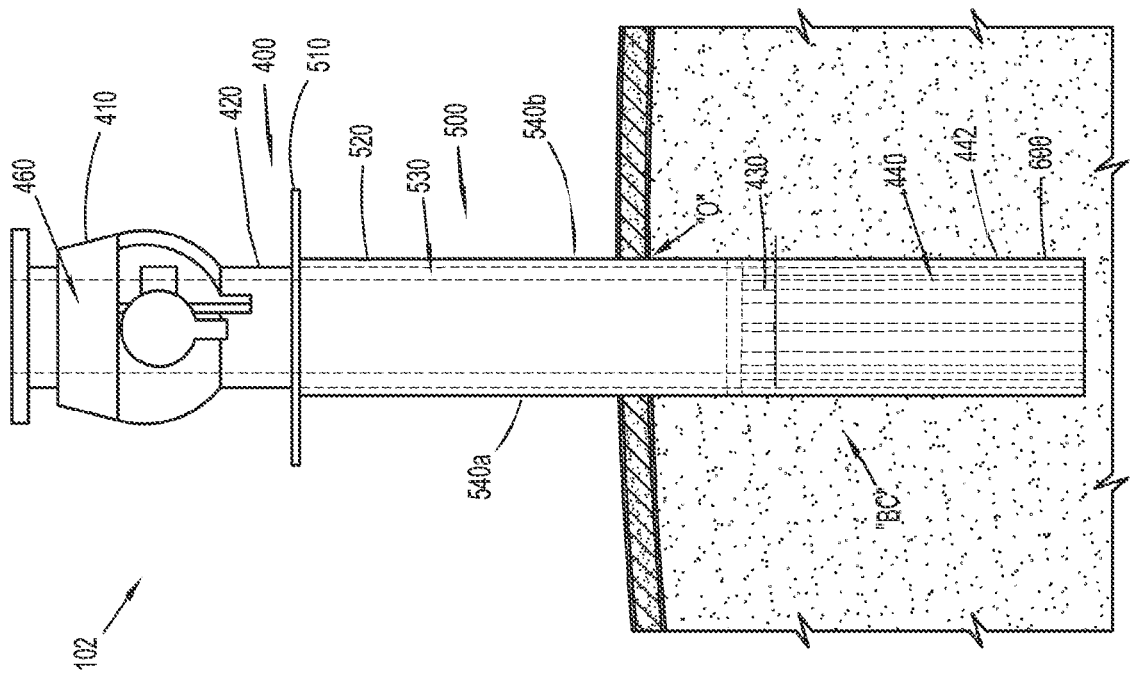
FIG. 3 is a side, longitudinal, partial cross-sectional view of another tissue specimen removal system provided in accordance with the present disclosure, disposed in an initial condition and extending through an opening in tissue into an internal body cavity.

Turning now to FIGS. 3 and 4, a specimen retrieval system 102 provided in accordance with another aspect of the present disclosure generally includes an inner assembly, such as, for example, an access cannula 400, an outer assembly, such as, for example, an introducer 500, and a containment bag 600.

With reference to FIG. 3, introducer 500 generally includes a proximal hub 510, an elongated tubular member 520, and a lumen 530 extending through proximal hub 510 and elongated tubular member 520. Lumen 530 of introducer 500 defines a suitable diameter configured to enable positioning of access cannula 400 and containment bag 600 therein. In embodiments, introducer 500 is provided with a first introducer portion 540a and a second introducer portion 540b that may be selectively coupled to form introducer 500 and selectively decoupled to form discrete first and second introducer portions 540a, 540b. It is contemplated that first and second introducer portions 540a, 540b may be releasably coupled via snap-fit or other suitable engagement(s).

In an initial condition (FIG. 3) of specimen retrieval system 102, with access cannula 400 and containment bag 600 disposed within lumen 530 of introducer 500, elongated tubular member 520 of introducer 500 is configured to extend through surgically created or naturally occurring opening "O" into the internal body cavity "BC" such that at least a portion of elongated tubular member 520, with access cannula 400 and containment bag 600 disposed therein, is positioned within internal body cavity "BC." As detailed below, once access cannula 400 and containment bag 600 are sufficiently disposed within internal body cavity "BC," introducer 500 may be disassembled into discrete first and second introducer portions 540a, 540b and removed from within internal body cavity "BC" and about access cannula 400 to transition specimen retrieval system 102 towards a deployed condition (FIG. 4).

Access cannula 400 may be similar to and/or include any of the features of access cannula 100 (FIGS. 1A and 1B), detailed above. Access cannula 400 generally includes a proximal hub 410, an elongated tubular member 420, an open distal mouth 430, and a port guard assembly 440. A lumen 460 extends through proximal hub 410 and elongated tubular member 420, in communication with open distal mouth 430.

With reference to FIG. 4, port guard assembly 440 includes a plurality of engagement fingers 442 configured as cantilever springs. Engagement fingers 442 are arranged radially-spaced about elongated tubular member 420 of access cannula 400 and extend distally therefrom. More specifically, engagement fingers 442 each include a fixed end 442a and a free end 442b. Fixed ends 442a of engagement fingers 442 are fixed to the exterior surface of elongated tubular member 420 adjacent open distal mouth 430 and extend distally to free ends 442b thereof. Free ends 442b of engagement fingers 442 extend distally beyond open distal mouth 430 of elongated tubular member 420 and are biased radially-outwardly from elongated tubular member 420. It is contemplated that any suitable number of engagement fingers 442 may be provided. Engagement fingers 442 may be formed from a spring-metal, e.g., spring steel, although other suitable materials, e.g., nitinol, may also be used.

In the initial condition (FIG. 3) of specimen retrieval system 102, wherein elongated tubular member 420 of access cannula 400 is disposed within lumen 530 of introducer 500, introducer 400 retains engagement fingers 442, against their bias, in a contracted configuration, wherein free ends 442b of engagement fingers 442 extend alongside one another, thus enabling engagement fingers 442 and elongated tubular member 420 to fit within lumen 530 of introducer 500. In the deployed condition (FIG. 4) of specimen retrieval system 102, introducer 500 is disassembled into discrete first and second introducer portions 540a, 540b and removed from about elongated tubular member 420, thus enabling engagement fingers 442 to return under bias towards their at-rest position, wherein free ends 442b of engagement fingers 442 are radially-outwardly spaced from elongated tubular member 420 to define an umbrella-like configuration. In embodiments, it is contemplated that port guard assembly 440 may be a stand-alone device, separate from access cannula 400, or may be connectable to access cannula 400 for use therewith or therewithout. In embodiments, port guard assembly 440 may be inserted through access cannula 440 until engagement fingers 442 extend distally from open distal mouth 430 to define the umbrella-like configuration described above.

Referring to FIGS. 3 and 4, containment bag 600 may be similar to and/or include any of the features of containment bag 300 (FIGS. 1A and 1B), detailed above. Containment bag 600 generally includes an outer surface 620a, an inner surface 620b, and a cavity "C" defined by inner surface 620b and configured to enable positioning of a tissue specimen(s) therein. Further, containment bag 600 includes an open end portion 610 configured to receive at least a portion of access cannula 400 and port guard assembly 440 thereof within cavity "C" of containment bag 600.

Containment bag 600 is configured for positioning, in the initial condition (FIG. 3) of specimen retrieval system 102, in the annular space defined between elongated tubular member 520 of introducer 500 and elongated tubular member 420 of access cannula 400, although a portion of containment bag 600 may extend proximally from both introducer 500 and access cannula 400 in the initial condition of specimen retrieval system 102. In the deployed condition (FIG. 4) of specimen retrieval system 102, containment bag 600 is deployed into the internal body cavity "BC" under urging from engagement fingers 442 of access cannula 400 and is unfurled, thus presenting containment bag 600 to enable positioning of tissue specimen(s) similar to tissue specimen "S" (FIGS. 2A and 2B) therein. Containment bag 600 may alternatively be separately positioned within the internal body cavity "BC" and thereafter engaged with access cannula 400.

In the deployed condition (FIG. 4) of specimen retrieval system 102, similar to port guard assembly 240 (FIG. 2), engagement fingers 442 of port guard assembly 440 of access cannula 400 are configured to engage a top portion 630 of containment bag 600, adjacent open end portion 610, and to urge top portion 630 of containment bag 600 radially outwardly to inhibit top portion 630 of containment bag 600 from collapsing about open distal mouth 430 of access cannula 400. As such, port guard assembly 440 is similarly configured to serve as a spacer between top portion 630 of containment bag 600 and open distal mouth 430 of access cannula 400 such that, a surgical instrument similar to surgical instrument 2 (FIG. 2B) e.g., morcellator or another cutting device, inserted through access cannula 400, and into cavity "C" of containment bag 600, is inhibited from inadvertently cutting or tearing containment bag 600. In addition to serving as a spacer, engagement fingers 442 also serve as guards to deflect surgical instrument 2 (FIG. 2B) should surgical instrument 2 stray towards inhibited top portion 630 of containment bag 600.

Containment, breakdown, and removal of the tissue specimen "S" (FIG. 2B) using containment bag 600 may be accomplished similarly as detailed above with regard to specimen retrieval system 101 (FIGS. 2A and 2B). Further, similarly as detailed above with regard to specimen retrieval system 101 (FIGS. 2A and 2B), some or all of the above may be performed under observation using visualization device 8 (FIG. 2B).

Figure 5:
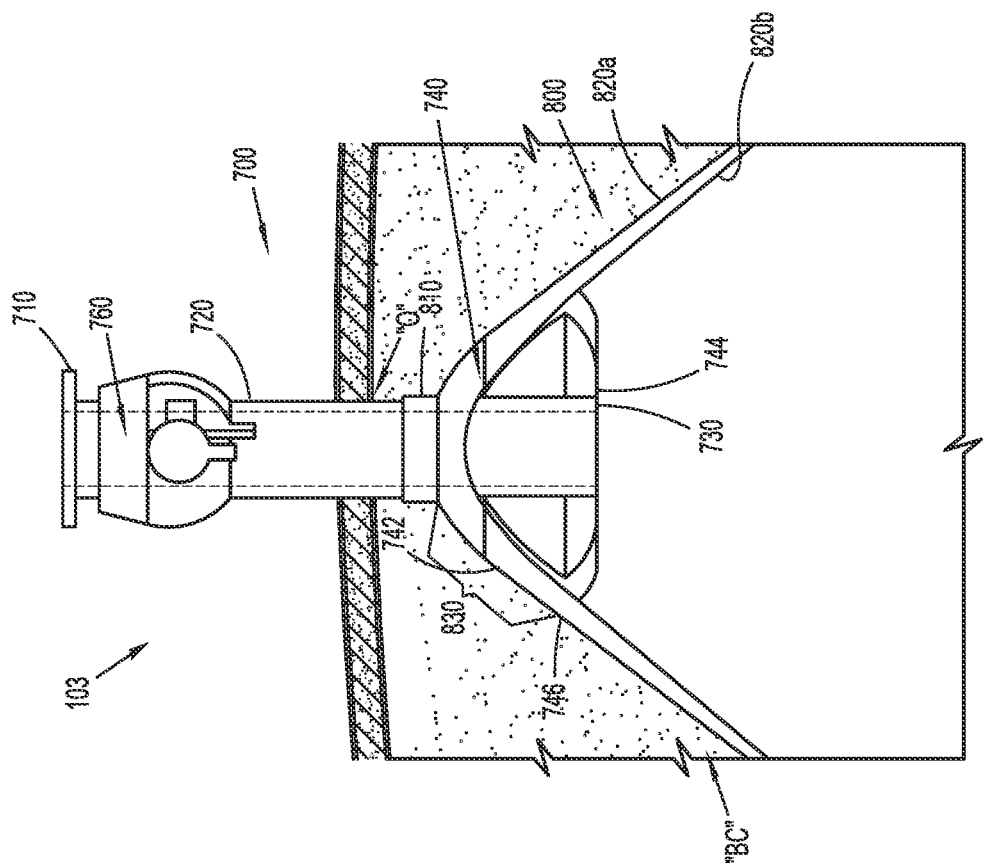
FIG. 5 is a side, longitudinal, partial cross-sectional view of another tissue specimen removal system provided in accordance with the present disclosure, disposed in an initial condition and extending through an opening in tissue into an internal body cavity.
Figure 6:
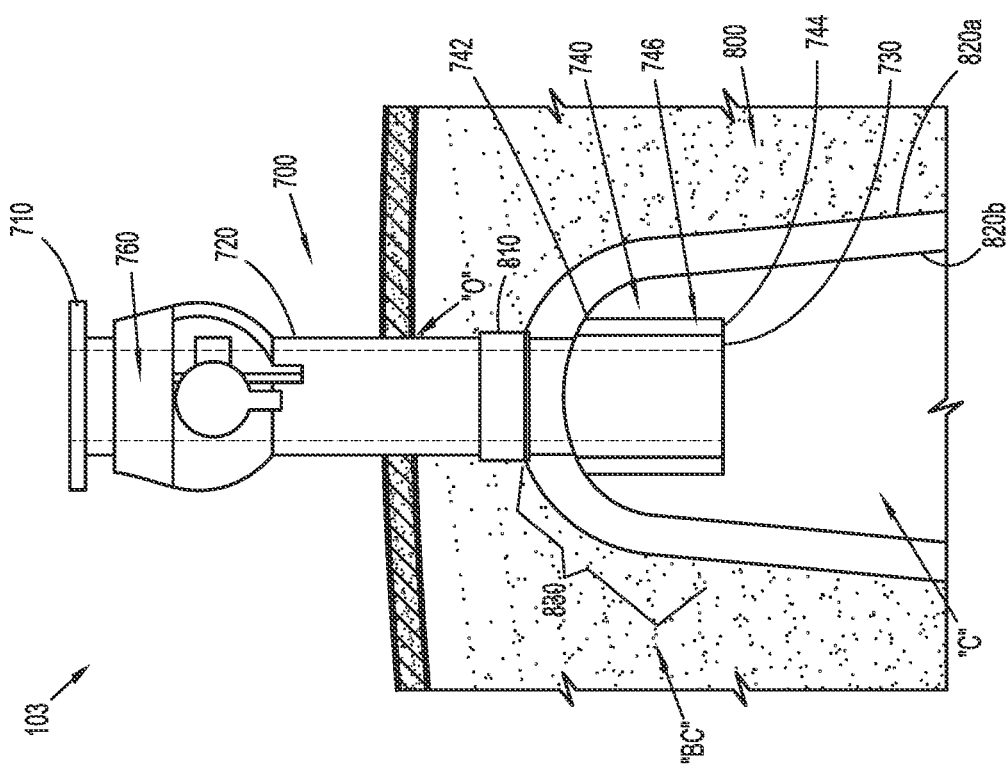
FIG. 6 is a side, longitudinal, partial cross-sectional view of the tissue specimen removal system of FIG. 5, disposed in a deployed condition and extending through an opening in tissue into an internal body cavity.

Turning now to FIGS. 5 and 6, a specimen retrieval system 103 provided in accordance with another aspect of the present disclosure generally includes an access cannula 700 and a containment bag 800.

Access cannula 700 may be similar to and/or include any of the features of access cannulas 100, 400 (FIGS. 1A-4), detailed above. Access cannula 700 generally includes a proximal hub 710, an elongated tubular member 720, an open distal mouth 730, and a port guard assembly 740. A lumen 760 extends through proximal hub 710 and elongated tubular member 720, in communication with open distal mouth 730.

Port guard assembly 740 includes an inflatable member, such as, for example, a balloon 742 fixed to the exterior surface of elongated tubular member 720 adjacent open distal mouth 730. More specifically, balloon 742 defines a donut-shaped configuration defining a lumen 744 configured to receive a portion of elongated tubular member 720 adjacent open distal mouth 730. Elongated tubular member 720 may be fixed within lumen 744 of balloon 742 using an adhesive or other suitable methods. In embodiments, an interior cavity 746 of balloon 742 is in fluid communication with lumen 760 of elongated tubular member 720 via lumen 744 such that balloon 742 is selectively inflatable. Accordingly, balloon 742 may be transitioned between a deflated configuration when specimen retrieval system 103 is in an initial condition (FIG. 5) and an inflated configuration when specimen retrieval system 103 is in a deployed condition (FIG. 6).

Containment bag 800 may be similar to and/or include any of the features of containment bags 300, 600 (FIGS. 1A-4), detailed above. Containment bag 800 generally includes an outer surface 820a, an inner surface 820b, and a cavity "C" defined by inner surface 820b and configured to enable positioning of tissue specimen(s) similar to tissue specimen "S" (FIGS. 2A and 2B) therein. Further, containment bag 800 includes an open end portion 810 configured to receive at least a portion of access cannula 700 and port guard assembly 740 thereof within cavity "C" of containment bag 800.

In the deployed condition (FIG. 6) of specimen retrieval system 103, similar to port guard assemblies 240, 440 (FIGS. 1B and 4), balloon 742 of port guard assembly 740 is configured to urge a top portion 830 of containment bag 800 radially outwardly, thus inhibiting top portion 830 from collapsing about open distal mouth 730 of access cannula 700. More specifically, as balloon 742 is inflated towards the deployed condition (FIG. 6), balloon 742 is configured to engage inner surface 820b adjacent top portion 830 and urge top portion 830 radially outwardly to increase the annular space between open distal mouth 730 of access cannula 700 and top portion 830 of containment bag 800. As such, port guard assembly 740 is similarly configured to act as a spacer between top portion 830 of containment bag 800 and open distal mouth 730 of access cannula 700 such that a surgical instrument similar to surgical instrument 2 (FIG. 2B) e.g., morcellator or another cutting device, inserted through access cannula 700, and into cavity "C" of containment bag 800, is inhibited from cutting or tearing containment bag 800.

In embodiments, specimen retrieval system 103 may include an introducer (not shown) similar to introducer 500 (FIG. 3) to facilitate insertion of access cannula 700 and containment bag 800 into internal body cavity "BC" via surgically created or naturally occurring opening "O" in the initial condition (FIG. 5) of specimen retrieval system 103.

Once the tissue specimen "S" (FIG. 2B) is sufficiently broken down and removed from containment bag 800, balloon 724 may be deflated (fully or partially) to return specimen retrieval system 103 towards the initial condition (FIG. 5), wherein top portion 830 of containment bag 800 is contracted about open distal mouth 730 of access cannula 700. Thereafter, access cannula 700 and containment bag 800 may be withdrawn together, or separately, from within internal body cavity "BC."

In embodiments, containment, breakdown, and removal of the tissue specimen "S" (FIG. 2B) using containment bag 800 may be accomplished similarly as detailed above with regard to specimen retrieval system 101 (FIGS. 2A and 2B). Further, similarly as detailed above with regard to specimen retrieval system 101 (FIGS. 2A and 2B), some or all of the above may be performed under observation using visualization device 8 (FIG. 2B).

Figure 8:
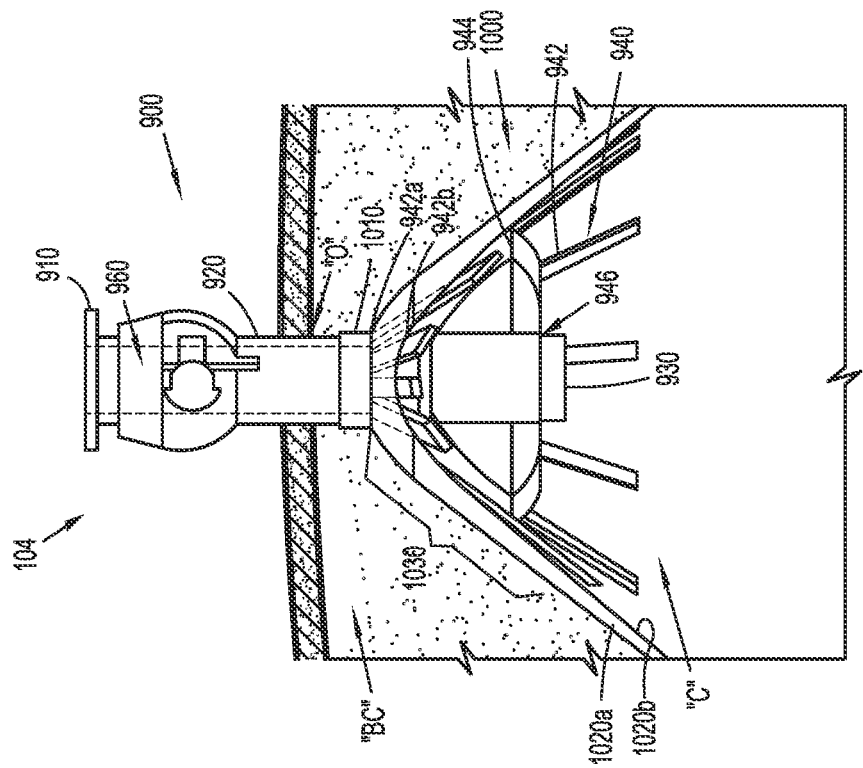
FIG. 8 is a side, longitudinal, partial cross-sectional view of the tissue specimen removal system of FIG. 7, disposed in a deployed condition and extending through an opening in tissue into an internal body cavity.
Figure 7:
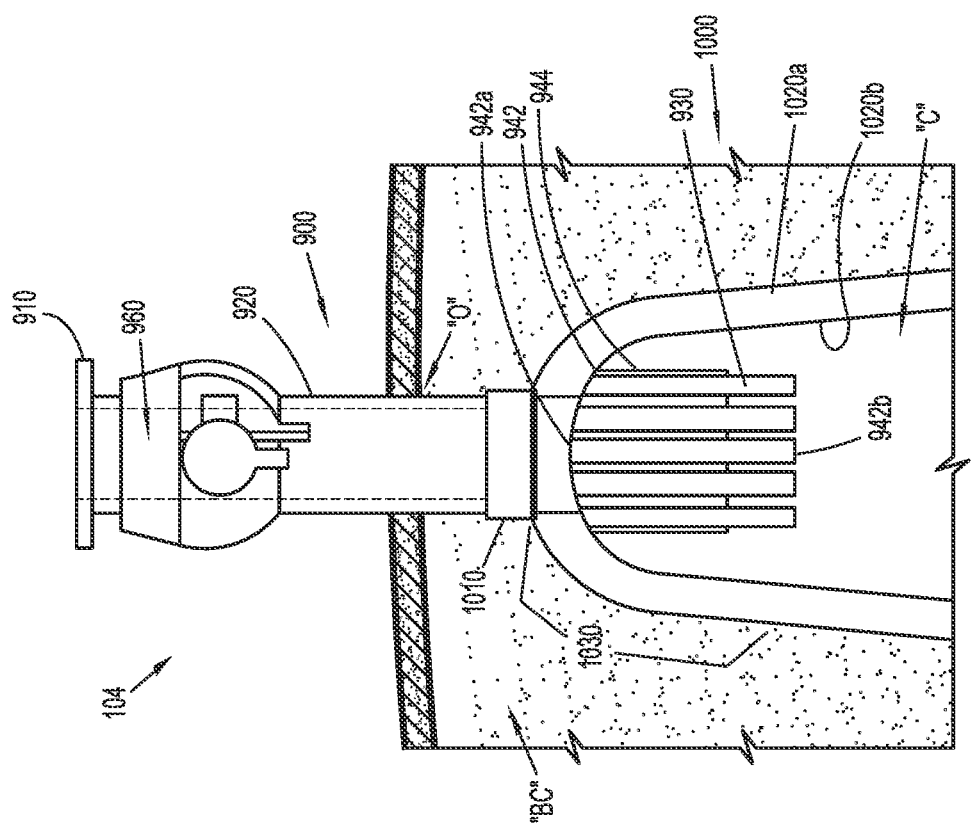
FIG. 7 is a side, longitudinal, partial cross-sectional view of another tissue specimen removal system provided in accordance with the present disclosure, disposed in an initial condition and extending through an opening in tissue into an internal body cavity.

Turning now to FIGS. 7 and 8, a specimen retrieval system 104 provided in accordance with another aspect of the present disclosure generally includes an access cannula 900 and a containment bag 1000.

Access cannula 900 may be similar to and/or include any of the features of access cannulas 100, 400, 700 (FIGS. 1A-6), detailed above. Access cannula 900 generally includes a proximal hub 910, an elongated tubular member 920, an open distal mouth 930, and a port guard assembly 940. A lumen 960 extends through proximal hub 910 and elongated tubular member 920, in communication with open distal mouth 930.

Port guard assembly 940 may be similar to and/or include any of the features of port guard assemblies 440, 740 (FIGS. 4 and 6), as detailed above. Port guard assembly 940 generally includes a plurality of engagement fingers 942 and an inflatable member, such as, for example, a balloon 944. Engagement fingers 942 each include a fixed end 942a, hingedly coupled to the exterior surface of elongated tubular member 920, and extending distally to a free end 942b.

Balloon 944 defines a donut-shaped configuration and includes a lumen 946 configured to fixedly receive a portion of elongated tubular member 920. Similar to balloon 742, balloon 944 is configured to be manipulated between a deflated configuration when specimen retrieval system 104 is in an initial condition (FIG. 7) and an inflated configuration when specimen retrieval system 104 is in the deployed condition (FIG. 8). Balloon 944 is disposed about elongated tubular member 920 at a position distal to fixed ends 942a of engagement fingers 942 such that engagement fingers 942 extend distally along the exterior surface of balloon 944 to free ends 942b.

In the initial condition (FIG. 7) of specimen retrieval system 104, balloon 944 is deflated and free ends 942b of engagement fingers 942 extend alongside one another over the exterior surface of balloon 944. In the deployed condition (FIG. 8) of specimen retrieval system 104, balloon 944 is inflated and engages the engagement fingers 942 disposed on the exterior surface thereof. As such, engagement fingers 942 are urged radially-outwardly from elongated tubular member 920 with the expansion of balloon 944.

Containment bag 1000 may be similar to and/or include any of the features of containment bags 300, 600, 800 (FIGS. 1A-6), detailed above. Containment bag 1000 generally includes an outer surface 1020a, an inner surface 1020b, and a cavity "C" defined by inner surface 1020b and configured to enable positioning of tissue specimen(s) similar to tissue specimen "S" (FIGS. 2A and 2B) therein.

Further, containment bag 1000 includes an open end portion 1010 configured to receive at least a portion of access cannula 900 and port guard assembly 940 thereof within cavity "C" of containment bag 1000.

In the deployed condition (FIG. 8) of specimen retrieval system 104, similar to port guard assemblies 240, 440, 740 (FIGS. 2, 4, and 6), port guard assembly 940 is configured to prevent a top portion 1030 of containment bag 1000, towards open end portion 1010, from collapsing about open distal mouth 930 of access cannula 900. More specifically, as balloon 944 is inflated towards the deployed condition (FIG. 8), balloon 944 urges engagement fingers 942 radially outwardly from elongated tubular member 920 such that, engagement fingers 942 engage inner surface 1020b adjacent top portion 1030 to urge top portion 1030 radially outwardly, thereby increasing the annular space between open distal mouth 930 of access cannula 900 and top portion 1030 of containment bag 1000.

As such, port guard assembly 940 is similarly configured to provide a spacer between top portion 1030 of containment bag 1000 and open distal mouth 930 of access cannula 900 such that, a surgical instrument similar to surgical instrument 2 (FIG. 2B) e.g., morcellator or another cutting device, inserted through access cannula 900, and into cavity "C" of containment bag 1000, is inhibited from cutting or tearing containment bag 1000.

In embodiments, specimen retrieval system 104 may include an introducer (not shown) similar to introducer 500 (FIG. 3) such that access cannula 900 and containment bag 1000 may be disposed within internal body cavity "BC" via surgically created or naturally occurring opening "O" in the initial condition (FIG. 7) of specimen retrieval system 104.

Once the tissue specimen "S" (FIG. 2B) is sufficiently broken down and removed from containment bag 1000, balloon 944 may be deflated (fully or partially) to return specimen retrieval system 104 towards the initial condition (FIG. 7), wherein engagement fingers 942 are in the contracted configuration and extend alongside one another over the exterior surface of balloon 944 and top portion 1030 of containment bag 1000 is contracted about open distal mouth 930 of access cannula 900. Thereafter, access cannula 900 and containment bag 1000 may be withdrawn together, or separately, from within internal body cavity "BC."

In embodiments, containment, breakdown, and removal of the tissue specimen "S" (FIG. 2B) using containment bag 1000 may be accomplished similarly as detailed above with regard to specimen retrieval system 101 (FIGS. 2A and 2B). Further, similarly as detailed above with regard to specimen retrieval system 101 (FIGS. 2A and 2B), some or all of the above may be performed under observation using visualization device 8 (FIG. 2B).

Turning now to FIGS. 9-12, a specimen retrieval system 105 provided in accordance with another aspect of the present disclosure generally includes an outer assembly, such as, for example, an access cannula 2000, an inner assembly, such as, for example, a deployment cannula 3000, and a containment bag 4000.

Access cannula 2000 may be similar to and/or include any of the features of access cannulas 100, 400, 700, 900 (FIGS. 1-8), detailed above. Access cannula 2000 generally includes a proximal hub 2010, an elongated tubular member 2020, an open distal mouth 2030, and a port guard assembly 2040. A lumen 2060 extends through proximal hub 2010 and elongated tubular member 2020, in communication with open distal mouth 2030.

Deployment cannula 3000 may be similar to and/or include any of the features of deployment cannula 200

(FIGS. 1A and 1B), detailed above. Deployment cannula 3000 generally includes a proximal hub 3010, an elongated core, such as, for example, a tubular member 3020, an open distal mouth 3030, and a camming boss 3040. In embodiments, camming boss 3040 is configured as a plurality of radially spaced-apart protrusions or tabs disposed on the exterior surface of tubular member 3020 towards open distal mouth 3030. A lumen 3060 extends through proximal hub 3010 and tubular member 3020, in communication with open distal mouth 3030.

Deployment cannula 3000 is configured for slidable positioning within lumen 2060 of access cannula 2000 and may be positioned therein in an initial condition (FIG. 9) during manufacturing or may be inserted into access cannula 2000 by a user.

Proximal hub 3010 of deployment cannula 3000 is configured to remain externally-disposed relative to the internal surgical site and access cannula 2000. More specifically, in an initial condition (FIG. 9) of specimen retrieval system 105, proximal hub 3010 of deployment cannula 3000 is positioned proximally adjacent proximal hub 2010 of access cannula 2000. In a deployed condition (FIG. 10), on the other hand, proximal hub 3010 of deployment cannula 3000 is proximally-spaced from proximal hub 2010 of access cannula 2000.

Figure 12:
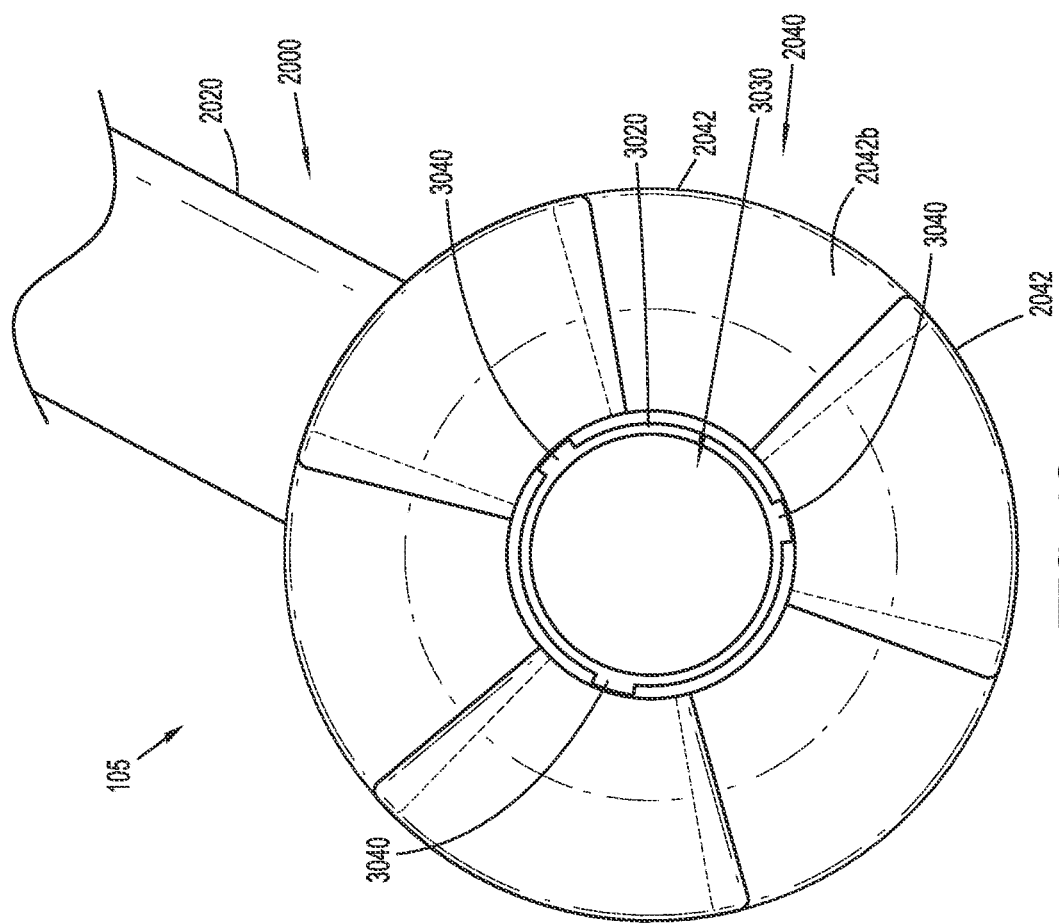
FIG. 12 is a bottom, perspective view of the end portion of the access cannula and the deployment cannula of FIG. 11, disposed in the deployed condition.
Figure 11:
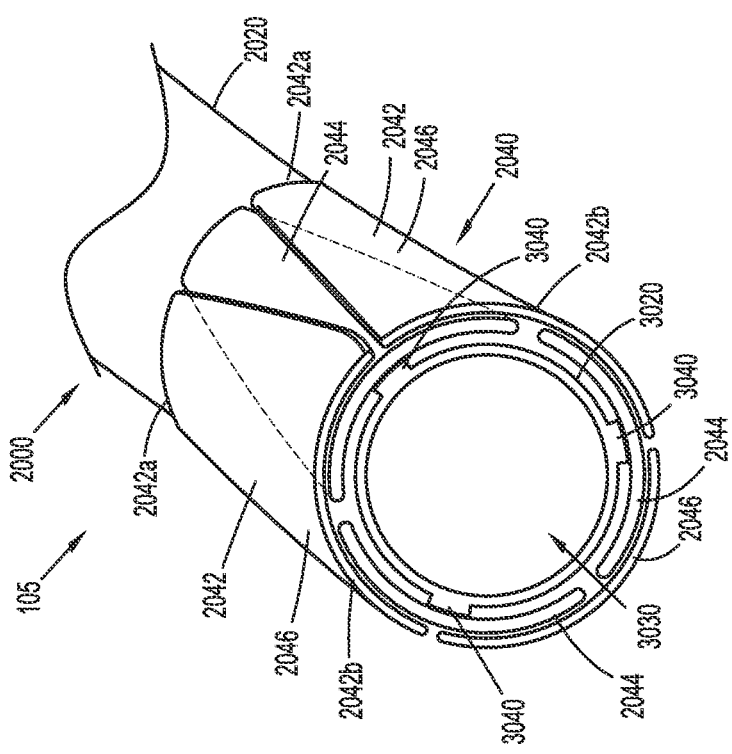
FIG. 11 is a bottom, perspective view of an end portion of an access cannula and a deployment cannula of the system of FIG. 9, disposed in the initial condition.

With reference to FIGS. 11 and 12, port guard assembly 2040 includes a plurality of petals 2042 that are folded to overlap with adjacent petals 2042. Petals 2042 each include a fixed end 2042a, having a living hinge (or other suitable hinge structure) coupled to the exterior surface of elongated tubular member 2020 adjacent open distal mouth 2030 (FIGS. 9 and 10), and extending distally to a free end 2042b. In the initial condition (FIG. 9) of specimen retrieval system 105, petals 2042 are retained in a contracted configuration, wherein petals 2042 extend alongside the exterior of tubular member 3020 of deployment cannula 3000 (FIG. 11). In embodiments, in the initial condition (FIG. 9) of specimen retrieval system 105, petals 2042 are arranged to include a base layer of petals 2044 (FIG. 11) disposed adjacent the exterior of tubular member 3020 and a top layer of petals 2046 (FIG. 11) folded over and disposed adjacent the base layer of petals 2044 in offset orientation relative to the base layer. As deployment cannula 3000 is moved proximally relative to access cannula 2000 towards the deployed condition (FIG. 10) of specimen retrieval system 105, camming boss 3040 cams proximally along the interior surface of the base layer of petals 2044 of petals 2042 towards fixed ends 2042a thereof. The movement of camming boss 3040 increasingly urges the base layer of petals 2044 radially outwardly such that the overlapping top layer of petals 2046 are likewise increasing urged radially outwardly. As such, petals 2042 expand outward from the exterior surface of tubular member 3020 and are radially-outwardly spaced from elongated tubular member 2020 of access cannula 2000 (FIG. 12).

With reference again to FIGS. 9 and 10, containment bag 4000 may be similar to and/or include any of the features of containment bags 300, 600, 800, 1000 (FIGS. 1-8), detailed above. Containment bag 4000 generally includes an outer surface 4020a, an inner surface 4020b, and a cavity "C" defined by inner surface 4020b and configured to enable positioning of tissue specimen(s) similar to tissue specimen "S" (FIGS. 2A and 2B) therein. Further, containment bag 4000 includes an open end portion 4010 configured to receive at least a portion of access cannula 2000, port guard assembly 2040 thereof, and deployment cannula 3000 within cavity "C" of containment bag 4000.

In the deployed condition (FIG. 10) of specimen retrieval system 105, similar to port guard assemblies 240, 440, 740, 940 (FIGS. 1B, 4, 6, and 8), port guard assembly 2040 is configured to urge a top portion 4030 of containment bag 4000 radially outwardly, thus inhibiting top portion 4030 of containment bag 4000 from collapsing about open distal mouth 2030 of access cannula 2000. More specifically, as petals 2042 are expanded towards the deployed condition (FIG. 10), petals 2042 engage inner surface 4020b adjacent top portion 4030 and urge top portion 4030 radially outwardly to increase the annular space between open distal mouth 2030 of access cannula 2000 and top portion 4030 of containment bag 4000.

As such, port guard assembly 2040 is similarly configured to provide a spacer between top portion 4030 of containment bag 4000 and open distal mouth 2030 of access cannula 2000 such that, a surgical instrument similar to surgical instrument 2 (FIG. 2B) e.g., morcellator or another cutting device, inserted through deployment cannula 3000 and, and into cavity "C" of containment bag 4000, is inhibited from cutting or tearing containment bag 4000.

In embodiments, specimen retrieval system 105 may include an introducer (not shown) similar to introducer 500 (FIG. 3) such that access cannula 2000, deployment cannula 300, and containment bag 4000 may be disposed within internal body cavity "BC" via surgically created or naturally occurring opening "O" in the initial condition (FIG. 9) of specimen retrieval system 105.

Containment, breakdown, and removal of the tissue specimen "S" (FIG. 2B) using containment bag 4000 may be accomplished similarly as detailed above with regard to specimen retrieval system 101 (FIGS. 2A and 2B). Further, similarly as detailed above with regard to specimen retrieval system 101 (FIGS. 2A and 2B), some or all of the above may be performed under observation using visualization device 8 (FIG. 2B).

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for removal of a tissue specimen from an internal body cavity, comprising:
    an access cannula including a first elongated tubular member and a port guard assembly having a plurality of engagement fingers, each engagement finger of the plurality of engagement fingers engaged to a distal end portion of the first elongated tubular member at a fixed end of the engagement finger and extending to a free end of the engagement finger, wherein, in an initial condition, the plurality of engagement fingers is retained in a contracted configuration wherein each engagement finger of the plurality of engagement fingers extends alongside the first elongated tubular member, and wherein, in a deployed condition, the free end of each engagement finger of the plurality of engagement fingers extends radially outwardly from the first elongated tubular member; and a containment bag including an open end portion engaged about the distal end portion of the first elongated tubular member of the access cannula, wherein, in the initial condition, a portion of the containment bag is positioned adjacent the first elongated tubular member, and wherein, in the deployed condition, the portion of the containment bag is engaged by the plurality of engagement fingers and urged radially outwardly such that the portion is spaced-apart from the first elongated tubular member.

2. The system according to claim 1, further comprising an introducer including a second elongated tubular member having a first introducer portion configured to selectively couple to a second introducer portion to define a lumen extending through the second elongated tubular member, wherein the lumen is configured to selectively retain the access cannula and the containment bag in the initial condition.

3. The system according to claim 2, wherein the plurality of fingers is biased radially-outwardly from the first elongated tubular member such that, in the initial condition, the plurality of fingers is retained in the contracted configuration in the lumen of the introducer against the bias of the plurality of fingers.

4. The system according to claim 3, wherein, in the deployed condition, the first introducer portion is configured to selectively decouple from the second introducer portion such that, the access cannula is released from the lumen of the introducer and the free end of each engagement finger of the plurality engagement fingers is radially-outwardly returned under the bias of the plurality of engagement fingers.

5. The system according to claim 4, wherein, in the initial condition, the containment bag is disposed within an annular space defined within the lumen of the introducer between the second elongated tubular member and the first elongated tubular member, and wherein, in the deployed condition, the containment bag is deployed from the lumen of the introducer under the bias of the plurality of engagement fingers.

6. The system according to claim 1, wherein the port guard assembly further includes an inflatable member disposed on the first elongated tubular member and engaged with the plurality of engagement fingers, the inflatable member having a deflated configuration in the initial condition and an inflated configuration in the deployed condition, wherein, in the inflated configuration, the inflatable member is configured to engage the plurality of engagement fingers and urge the free ends of each of plurality engagement fingers radially-outwardly.

7. The system according to claim 6, wherein the inflatable member is disposed on the first elongated tubular member distal to the fixed ends of each engagement finger of the plurality of engagement fingers such that the plurality of engagement fingers extends distally along an exterior surface of the inflatable member.

8. The system according to claim 6, wherein the inflatable member includes a lumen defined therein configured to receive the elongated tubular member of the access cannula.

9. The system according to claim 8, wherein the inflatable member includes an interior cavity defined therein configured to be in fluid communication with the elongated tubular member of the access cannula such that the inflatable member is selectively inflatable via the access cannula.

10. A system for removal of a tissue specimen from an internal body cavity, comprising:
an access cannula including a first elongated tubular member and a port guard assembly having a plurality of engagement fingers, each engagement finger of the plurality of engagement fingers fixed to and extending from a distal end portion of the first elongated tubular member, each engagement finger of the plurality of engagement fingers defining a free end, wherein, in an initial condition, the plurality of engagement fingers is retained in a contracted configuration, and wherein, in a deployed condition, the free end of each engagement finger of the plurality of engagement fingers extends radially outwardly from the first elongated tubular member; and
a containment bag including an open end portion engaged about the distal end portion of the first elongated tubular member of the access cannula, wherein, in the initial condition, a portion of the containment bag is positioned adjacent the first elongated tubular member, and wherein, in the deployed condition, the portion of the containment bag is engaged by the plurality of engagement fingers and urged radially outwardly such that the portion is spaced-apart from the first elongated tubular member.

11. The system according to claim 10, wherein the port guard assembly further includes an inflatable member disposed on the first elongated tubular member and engaged with the plurality of engagement fingers, the inflatable member having a deflated configuration in the initial condition and an inflated configuration in the deployed condition, wherein, in the inflated configuration, the inflatable member is configured to engage the plurality of engagement fingers and urge the free ends of each of plurality engagement fingers radially-outwardly.

12. The system according to claim 11, wherein the inflatable member is disposed on the first elongated tubular member distal to the fixed ends of each engagement finger of the plurality of engagement fingers such that the plurality of engagement fingers extends distally along an exterior surface of the inflatable member.

13. The system according to claim 11, wherein the inflatable member includes a lumen defined therein configured to receive the elongated tubular member of the access cannula.

14. The system according to claim 13, wherein the inflatable member includes an interior cavity defined therein configured to be in fluid communication with the elongated tubular member of the access cannula such that the inflatable member is selectively inflatable via the access cannula.

\* \* \* \* \*